United States Patent [19]

Falkevich et al.

[11] Patent Number: 4,856,336
[45] Date of Patent: Aug. 15, 1989

[54] ULTRASONIC FLAW DETECTOR

[76] Inventors: Sergei A. Falkevich, 5 Parkovaya ulitsa, 52,kv.31; Mikhail V. Naumov, Sirenevy bulvar. 52,kv.143, both of Moscow; Jury M. Shkarlet, Lefortovsky val, 12,kv.40; Dmitry V. Sukhorukov, 2 Vladimirskaya ulitsa,50,korpus 2,kv.51, both of Moscow; Viktor N. Fedotov, ulitsa Lenina, 6a,kv.8., Moskovskaya oblast, Klimovsk; Jury I. Sazonov, Likhachevskoe shosse,10,kv.I89., Moskovskaya oblast Dolgoprudny, all of U.S.S.R.

[21] Appl. No.: 170,998
[22] PCT Filed: Apr. 30, 1986
[86] PCT No.: PCT/SU86/00044
  § 371 Date: Dec. 17, 1987
  § 102(e) Date: Dec. 17, 1987
[87] PCT Pub. No.: WO87/06704
  PCT Pub. Date: Nov. 5, 1987
[51] Int. Cl.$^4$ .................. G01N 29/00; G01N 29/04
[52] U.S. Cl. .......................... 73/598; 73/620; 73/626
[58] Field of Search ............... 73/598, 620, 622, 623, 73/624, 625, 626, 627, 628, 629

[56] References Cited

U.S. PATENT DOCUMENTS

| | | | |
|---|---|---|---|
| 4,043,321 | 8/1977 | Soldner et al. | 73/598 |
| 4,487,070 | 12/1984 | Gerling et al. | 73/620 |
| 4,542,653 | 9/1985 | Liu | 73/626 |
| 4,543,829 | 10/1985 | Lerch | 73/626 |

FOREIGN PATENT DOCUMENTS

| | | |
|---|---|---|
| 0114595 | 1/1984 | European Pat. Off. |
| 2243435 | 4/1975 | France |
| 463060 | 1/1973 | U.S.S.R. |
| 1146595 | 3/1985 | U.S.S.R. |
| 1170342 | 7/1985 | U.S.S.R. |
| 1185230 | 10/1985 | U.S.S.R. |

OTHER PUBLICATIONS

Falkevich, S. A., *Issledovanie lineinoi reshetki piezovibratoror s elektricheskim skanirovaniem*, 1979, Defektoskopia, No. 4, Moscow.

*Primary Examiner*—Stewart J. Levy
*Assistant Examiner*—Robert P. Bell
*Attorney, Agent, or Firm*—Burgess, Ryan & Wayne

[57] ABSTRACT

An ultrasonic flaw detector comprises channels for transmitting and receiving electrical signals. The transmission channel comprises a sync pulse generator (1) connected to a sonic pulse generator (2) and transmitting piezoelectric elements (3). The receiving channel comprises receiving piezoelectric elements (4), a radio-frequency pulse amplifier (6), a video detector (7), a control voltage generator (15), and horizontal-sweep and vertical-sweep generators (16 and 15) which are connected to a frequency divider (13). The output of the video amplifier (8) is connected to a multivibrator (10). The receiving channel also comprises three electronic switches (11, 12, and 5).

2 Claims, 3 Drawing Sheets

ULTRASONIC FLAW DETECTOR

FIELD OF THE INVENTION

This invention relates to means for inspection and analyses of materials by ultrasonic waves and, in particular, is concerned with ultrasonic flaw detectors.

BACKGROUND ART

Known in the art is an ultrasonic detector (A. K. Gurvich, I. N. Ermolov, Ultrazvukovoi kontrol svarnykh shvov, Tekhnika Publ., Kiev, 1972, p. 426) comprising a synchronizing signal generator connected to an acoustic pulse generator whose output is coupled to a piezoelectric crystal element whose output is connected to a recorder via a radio-frequency pulse amplifier, a video detector and a video amplifier, all coupled in series.

The piezoelectric element of this ultrasonic detector functions both as a transmitter and receiver of ultrasonic signals.

Sonic testing of a workpiece section is performed by longitudinal and transverse mechanical transportation of a fault locator. Test results are recorded.

The speed of testing is limited by the speed of mechanical movement of the fault locator and, also, by the necessity to maintain a reliable acoustical contact of this locator with the surface of the inspected workpiece. This affects the efficiency of the known ultrasonic flaw detector. In addition, in this ultrasonic detector any fault of acoustic contact has a substantial negative effect on the reliability of test results.

Known in the art is an ultrasonic flaw detector comprising transmitting and receiving channels, each channel having piezoelectric elements, a piezoelectric element switching unit inserted between the piezoelectric elements and an input of radio-frequency pulse amplifier, and a control unit coupled to this switching unit. These units are to switch groups of piezoelectric elements so as to connect them to the input of the radio-frequency pulse amplifier. This permits scanning of the ultrasonic beam along the piezoelectric transducer. The unit can be built around a multivibrator and electronic switches (FR, B, 2243435).

This ultrasonic flaw detector is deficient in that scanning is possible only along the piezoelectric transducer and not in a perpendicular plane, thus affecting the efficiency of ultrasonic testing.

Besides, the reliability of the ultrasonic detector and trustworthiness of test results are affected because the detector is equipped with only one and structurally complex unit for switching and control.

Also known in the art is an ultrasonic detector (SU, A, 463060) comprising an electrical signal transmission channel and an electrical signal receiving channel. The transmission channel comprises a synchronizing pulse generator whose output is connected to a an acoustic pulse generator connected, in turn, to transmitting piezoelectric elements.

The receiving channel comprises receiving piezoelectric elements and, connected in series, a radio-frequency pulse amplifier, a video detector, a video amplifier, and a recording device. This circuit is connected to a control voltage generator and coupled to receiving piezoelectric elements.

The synchronizing pulse generator is connected to a horizontal scanning generator coupled to a frequency divider having its output connected to a vertical scanning generator.

The receiving piezoelectric elements are spaced apart to a distance less than or equal to the length of the ultrasonic wave.

Sonic testing of a workpiece is performed by this prior art flaw detector by a narrow scanning beam, which is achieved by changing phases of ultrasonic oscillations of the receiving piezoelectric elements. The reflected echo signals are received and used to assess the quality of the workpiece. This ultrasonic flaw detector can record fault parameters in the scanning plane continuously throughout the testing period.

This ultrasonic flaw detector is deficient in that its efficiency is poor because test results are recorded even when no flaws are present. This means that the efficiency of this ultrasonic flaw detector depends on the recording speed, the recording being performed continuously over the entire tested zone irrespective of the presence or absence of flaws in the workpiece.

Besides, the inherent lag of the recording device combined with the high scanning speed of the ultrasonic beam inevitably results in omissions of faults and the reliability of testing is impaired.

Another factor affecting the reliability of testing in known flaw detectors consists in variations of sensitivity of receiving and transmitting piezoelectric elements during electric scanning. These variations can certainly be attributed to the decrease of their projection on the plane perpendicular to the ultrasonic beam, this decrease being the function of the cos $\theta$, where $\theta$ is the angle of the ultrasonic beam with respect to a normal to piezoelectric elements, and, also, to capacitive couplings of piezoelectric elements (Defektoskopia, No. 4, 1979, Moscow, S. A. Falkevich, Issledovanie lineinoi reshetki piezovibratorov s elektricheskim skanirovaniem, pp. 60–66).

DISCLOSURE OF THE INVENTION

The invention is to provide an ultrasonic flaw detector wherein the trustworthiness of testing is improved by using a new mode of sonic testing of a workpiece being inspected and recording a flaw only after an echo-pulse arrives.

This is achieved by an ultrasonic detector in which an electric signal transmitting channel comprises a synchronizing signal generator connected to a sonic pulse generator connected to at least one transmitting piezoelectric element, while an electric signal receiving channel comprises at least two receiving piezoelectric elements spaced apart from one another to a distance less than or equal to the ultrasonic wavelength, a radio-frequency pulse amplifier, a video detector, a video amplifier, and a recording device, all connected in series and coupled to a control voltage generator and to receiving piezoelectric elements, and also a horizontal-sweep generator connected to the synchronizing signal generator and a frequency divider whose output is connected to a vertical-sweep generator, according to the invention, an electric signal receiving channel comprises a multivibrator whose input is connected to an output of the video amplifier, a first electronic switch whose control input is connected to a first output of the multivibrator whose input is connected to the frequency divider and whose output is connected to the control voltage generator, a second electronic switch having its control input connected to the first output of the multivibrator, its input connected to the output of the transmitting piezoelectric element, and its output connected to an input of the radio-frequency pulse amplifier, and a third electronic switch having its control input connected to a second output of the multivibrator, its input connected to the output of the receiving piezoelectric element, and its output connected to the radio-frequency pulse amplifier.

It is advisable that the flaw detector should comprise a circuit for levelling the sensitivity of ultrasonic testing, having its input connected to an output of the video detector, its output connected to an input of the video amplifier, and its control input connected to the output of the control voltage generator.

BRIEF DESCRIPTION OF ACCOMPANYING DRAWINGS

The invention will now be described with reference to specific embodiments thereof and to accompanying drawings in which.

BEST MODE FOR CARRYING OUT THE INVENTION

The ultrasonic flaw detector is based on the principle of scanning ultrasonic radiation. It comprises two channels for transmitting and receiving electrical signals.

Figure 1:
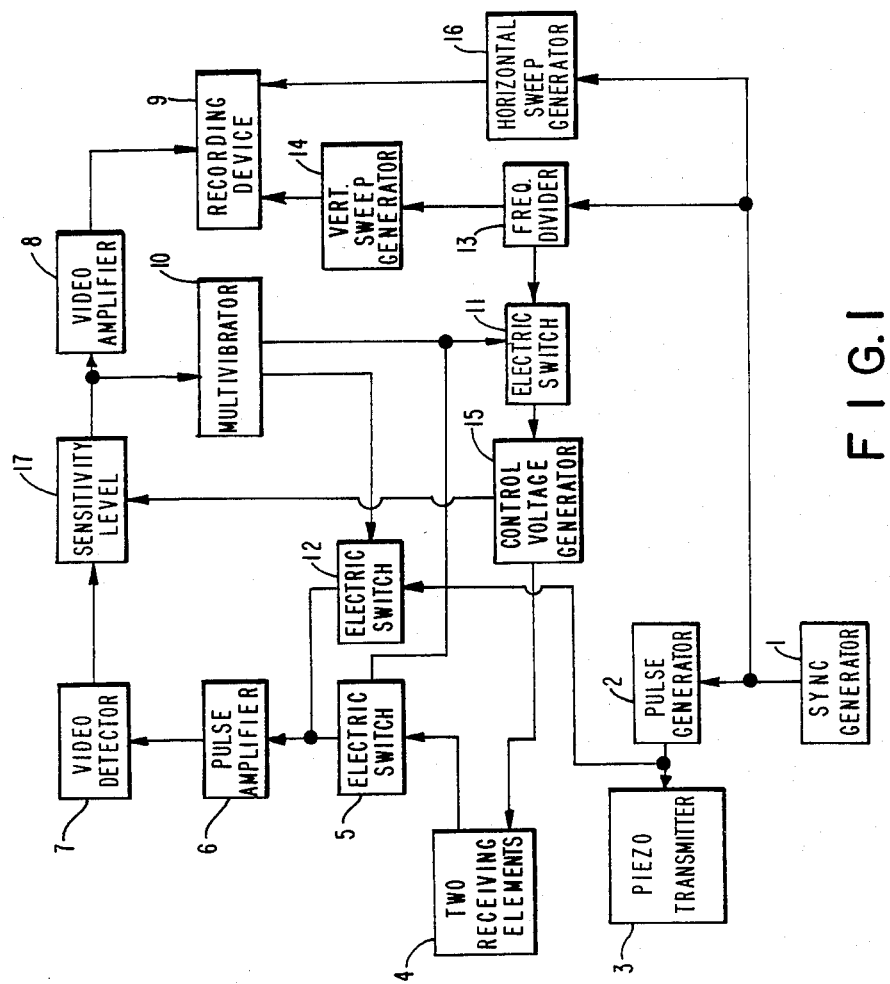
FIG. 1 shows a block diagram of an ultrasonic flaw detector, according to the invention.

The electrical signal transmitting channel comprises a synchronizing signal generator 1 (FIG. 1) connected to a sonic pulse generator 2. It also comprises at least one transmitting piezoelectric crystal element 3. The number of piezoelectric transmitting elements 3 is dictated by the size of the electric scanning sector and, in practical terms, can never exceed ten.

The electric signal receiving channel comprises at least two receiving piezoelectric elements 4 spaced apart to a distance less than or equal to the ultrasonic wavelength. The number of such receiving piezoelectric elements is dictated by the desired angle resolution and by the desired angle resolution and by the thickness of the workpiece being tested. It rarely exceeds 100.

The output of the last piezoelectric element 4 is connected to an input of an electronic switch 5 whose output is connected to the following series-connected units: a radio-frequency pulse amplifier 6, a video detector 7, a video amplifier 8, and a recording device 9.

The output of the video amplifier 8 is connected to an input of a multivibrator 10 having one output thereof connected to a control input of the electronic switch 5 and a control input of an electronic switch 11 and having another output connected to a control input of an electronic switch 12.

The receiving channel comprises a frequency divider 13 having its input connected to the sync generator 1, its first output connected to an input of the electronic switch 11 and its second output connected to an input of a vertical-sweep generator 14. The output of the electronic switch 11 is connected to a control voltage generator 15 having its output connected to the receiving piezoelectric elements 4.

Inputs of the recording device 9 are connected to an output of the vertical-sweep generator 14 and a horizontal-sweep generator 16.

The input of the electronic switch 12 is connected to an output of the sonic pulse generator 2, while the output thereof is joined with the output of the switch 5.

An input of the horizontal-sweep generator 16 is connected to the output of the sync generator 1.

The output of the video detector 7 is connected to a circuit 17 for levelling the sensitivity of ultrasonic testing, having its control input connected to the output of the control voltage generator 15 and its output to the input of the video amplifier 8.

Figure 2:
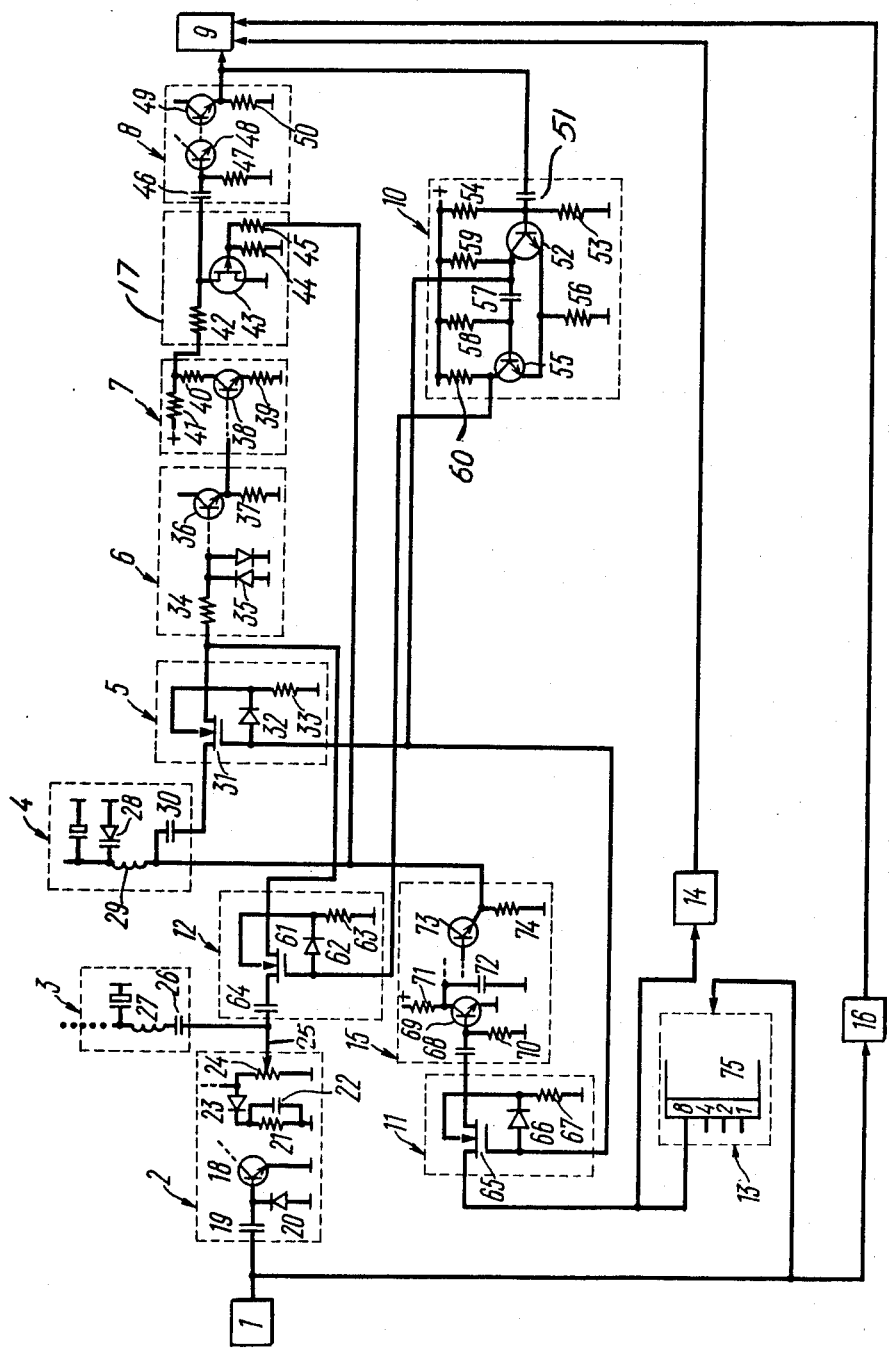
FIG. 2 shows a circuit diagram of an electric signal receiving channel of the ultrasonic flaw detector, according to the invention.

The circuit diagram of some units of the ultrasonic flaw detector is shown in FIG. 2.

The sonic pulse generator 2 comprises a transistor 18 (FIG. 2) whose base is connected to a capacitor 19 and a diode 20. The output circuit of the generator 2 comprises a resistor 21 coupled in parallel to a capacitor 22 which are both connected, via a diode 23, to a potentiometer 24. A contact arm of the potentiometer 24 is connected to a first transmitting piezoelectric element 3 via a blocking capacitor 26 and in inductance coil 27.

A varicap 28 is connected parallel to the last piezoelectric element 4 of the receiving channel via an inductance coil 29 and a blocking capacitor 30. This last piezoelectric element 4 is connected to the source of a field-effect transistor 31. A diode 32 is inserted between the control gate and substrate of the field-effect transistor 31, the substrate being connected to the ground via a resistor 33. The drain of the transistor 31 is connected to the input of the radio-frequency pulse amplifier 6 via a resistor 34 and limiting diodes 35.

The output stage of the rf pulse amplifier 6 is an emitter follower built around a transistor 36 with an emitter load 37. The output of the rf pulse amplifier 6 is connected to the input of the video detector 7. The emitter of a transistor 38 of the video detector 7 is grounded via a resistor 39, while the collector of the transistor 38 is connected to the positive terminal of the power source via the series-connected resistors 40 and 41.

The output of the video detector 7 is connected, via a resistor 42, to the drain of a field-effect transistor 43, while the control gate thereof is grounded via a resistor 44 and, also, connected to the output of the control voltage generator 15 via a resistor 45. The drain of the field-effect transistor 43 is connected, via a blocking capacitor 46, to the base of a transistor 48 of the video amplifier 8, which is connected to the ground via a resistor 47. The emitter of a transistor 49 of the output stage of the video pulse amplifier 8 is connected to the ground via a resistor 50 and to the input of the recording device 9.

The emitter of the transistor 49 is also connected, via a blocking capacitor, to the base of a transistor 52 of the multivibrator 10. The base of the transistor 52 is grounded via a resistor 53 and connected, via a resistor 54, to the positive terminal of the power source. Emitters of the transistors 52 and 55 are joined together and connected, via a resistor 56, to the ground. The base of the transistor 55 is connected to the collector of the transistor 52 via a blocking capacitor 57 and to the positive terminal of the power source via a resistor 58. The collector of the transistor 52 is connected, via a resistor 59, to the positive terminal of the power source. The collector of the transistor 55 is also connected to the positive terminal via a resistor.

The collector of the transistor 55 is connected to an insulated gate of a field-effect transistor 61 of the electronic switch 12. A diode 62 is inserted parallel to the gate of the field-effect transistor 61 and connected to ground via a resistor 63.

The source of the field-effect transistor 61 is connected via a capacitor 64 to the contact arm 25 of the potentiometer 24. The collector of the transistor 52 is connected to the gate of the field-effect transistor 31 of switch 5 and the gate of a field-effect transistor 65 of the switch 11.

A diode 66 is inserted parallel to the gate and drain of the field-effect transistor 65 and connected to ground via a resistor 67. The drain of the field-effect transistor 65 is connected, via a blocking capacitor 68, to the base of a transistor 69 of the control voltage generator 15. A resistor 70 is inserted between the base of the transistor 69 and "ground". The collector of the transistor 69 is connected, via a resistor 71, to the positive terminal of the power source and, via a capacitor 72, to ground. The emitter of a transistor 73 is connected to ground via a resistor 74 and to the inductor coil 29 of the receiving transducer 4.

The source of the field-effect transistor 65 is connected to an output of a microcircuit 75 of the frequency divider 13 and to an input of the vertical-sweep generator 14 whose output is connected to the recording device 9.

Other units and circuits of the herein disclosed ultrasonic flaw detector are made conventionally.

The ultrasonic flaw detector made according to the invention operates as follows.

Figure 3:
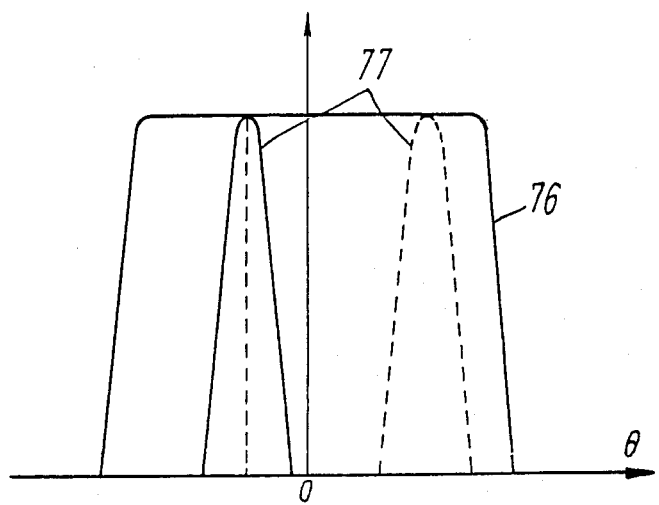
FIGS. 3 shows directivity patterns of transmitting and receiving piezoelectric elements of the ultrasonic flaw detector, according to the invention.

The generator 1 produces a sequence of sync pulses to be applied to the input of the sonic pulse generator 2. Sonic pulses are supplied to the transmitting piezoelectric elements 3 which produce a wide beam of the directional pattern 76 (FIG. 3) aimed at the workpiece to be inspected. When no echo signals ae produced by flaws, piezoelectric elements 3 operate as transmitters and receivers of ultrasonic oscillations. When a flaw occurs in the workpiece, echo signals are fed via the electronic switch 12 to the input of the radio-frequency pulse amplifier 6, are detected by the video detector 7, and are supplied, from the output of the video amplifier 8 to the input of the one-shot multivibrator 10. Output signals of the multivibrator 10 disable the switch 12 and close switches 5 and 11. When the electronic switch 11 becomes conductive, output signals of the frequency divider 13 are supplied to the input of the control voltage generator 15 whose signal controls the beam position of the receiving piezoelectric elements 4.

When the electronic switch 12 is disabled, transmitting piezoelectric elements 3 are disconnected from the input of the amplifier 6 and receiving piezoelectric elements 4 are connected thereto via the electronic switch 5 made conductive. In this condition, the transmitting piezoelectric elements 3 function as a projector while receiving piezoelectric elements 4 function as a receiver of ultrasonic oscillations. The number (k) of piezoelectric elements in the transmitting channel and the number (n) of piezoelectric elements in the receiving channel are selected in accordance with the following $$k = n\frac{\phi}{S},$$

where $\phi$ is the width of the directional pattern of the receiving array of the piezoelectric element 4, and S is the sector of electrical scanning of the transmitting array of the piezoelectric elements 4. With this number of transmitting piezoelectric elements 3, the width of the directional pattern 76 (FIG. 3) of the transmitting array of piezoelectric elements 3 is equal to the scanning sector of the receiving piezoelectric elements 4.

The voltage transfer ratio of the sensitivity levelling circuit 17 is the reverse function of sensitivity of the array of receiving piezoelectric elements 4 during scanning. This sensitivity levelling circuit 17 is to make constant the through transfer ratio of the receiving channel. Output control voltage of the generator 15 is the control voltage of the circuit 17.

This means that, when a flaw is detected, the flaw detector is automatically switched over to another mode of sounding, wherein a wide unscanned beam (76) is radiated and a narrow scanning beam 77 is used for reception. In this manner, the flaw is recorded starting from the moment an echo signal is received. A two-dimensional image of the flaw is obtained on the recording device 9 which may be a two-axis potentiometer or a cathode-ray tube. When the echo signal vanishes, the ultrasonic flaw detector automatically switches over to the former mode of operation.

The system permits recording a flaw only when echo pulses reflected from this flaw arrive and is intended to make the ultrasonic testing more reliable as compared with existing flaw detectors. Moreover, the ultrasonic flaw detector proposed herein uses only one amplifier for both the receiving and transmitting channels while in all known flaw detectors based on electrical scanning the number of amplifiers of the receiving and transmitting channels is equal to the number of receiving and transmitting piezoelectric elements. This feature also contributes to the reliability of ultrasonic testing.

INDUSTRIAL APPLICABILITY

This invention may be used for ultrasonic flaw detection in welded workpieces and for testing the continuity of material of metal structures in machine-building industry, construction of power installations and pipelines.

We claim:

1. An ultrasonic flaw detector wherein an electric signal transmitting channel comprises a sync generator (1) connected to a sonic pulse generator (2) connected to at least one transmitting piezoelectric element (3), while an electric signal receiving channel comprises at least two receiving piezoelectric elements (4) spaced apart to a distance less than or equal to the ultrasonic wavelength, and, connected in series, to a radio-frequency pulse amplifier (6), a video detector (7), a video amplifier (8), and a recording device (9), which are coupled to a control voltage generator (15) and to the receiving piezoelectric elements (4), as well as a horizontal-sweep generator (16) connected to the sync generator (1) and the latter connected to a frequency divider (13) whose output is connected to a vertical-sweep generator (14), characterized in that the electric signal receiving channel comprises a multivibrator (10) whose input is connected to an output of the video amplifier (8), a first electronic switch (11) having its control input connected to a first output of the multivibrator (10), its input to the frequency divider (13), and its output to the control voltage generator (15); a second electronic switch (12) having its control input connected to the first output of the multivibrator (10), its input connected to the input of the transmitting piezoelectric element (3), and its output connected to the input of the radio-frequency pulse amplifier (6); and a third electronic switch (5) having its control input connected to a second output of the multivibrator (10), its input connected to the output of the receiving piezoelectric element (4), and its output connected to the radio-frequency pulse amplifier (6).

2. An ultrasonic flaw detector as claimed in claim 1, characterized in that it comprises a circuit (17) for levelling the sensitivity of ultrasonic testing, having its input connected to an output of the video detector (7), its output connected to the input of the video amplifier (8), and its control input connected to the output of the control voltage generator (15).

* * * * *